(12) United States Patent
Dalmia et al.

(10) Patent No.: US 7,887,683 B2
(45) Date of Patent: *Feb. 15, 2011

(54) ELECTROCHEMICAL SENSOR COMPENSATED FOR RELATIVE HUMIDITY

(75) Inventors: Avinash Dalmia, Hamden, CT (US);
Otto J. Prohaska, Beacon Falls, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 1189 days.

This patent is subject to a terminal disclaimer.

(21) Appl. No.: 11/198,812

(22) Filed: Aug. 5, 2005

(65) Prior Publication Data
US 2005/0269203 A1 Dec. 8, 2005

Related U.S. Application Data

(63) Continuation of application No. 10/029,626, filed on Oct. 22, 2001, now Pat. No. 6,955,750.

(51) Int. Cl.
*G01N 27/407* (2006.01)
(52) U.S. Cl. .................................. 204/424; 204/426
(58) Field of Classification Search .............. 204/415, 204/421–429
See application file for complete search history.

(56) References Cited

U.S. PATENT DOCUMENTS

| | | | |
|---|---|---|---|
| 4,201,634 A * | 5/1980 | Stetter | 205/780.5 |
| 4,721,601 A | 1/1988 | Wrighton et al. | 422/68 |
| 4,781,798 A * | 11/1988 | Gough | 205/783 |
| 4,900,405 A * | 2/1990 | Otagawa et al. | 205/781 |
| 4,913,792 A * | 4/1990 | Nagata et al. | 204/412 |
| 4,929,313 A | 5/1990 | Wrighton | 205/778.5 |
| 5,006,786 A * | 4/1991 | McKubre et al. | 205/775.5 |
| 5,120,420 A * | 6/1992 | Nankai et al. | 204/403.11 |

(Continued)

FOREIGN PATENT DOCUMENTS

WO    WO 01/36957 A1    5/2001

OTHER PUBLICATIONS

Edwin W.H. Jager et al. "On chip microelectrodes for electrochemistry with moveable PPy bilayer actuators as working electrodes". Sensors and Actuators B, Elsevier Sequoia S.A., Lausanne, CH, vol. 56, 1-2, Jul. 1, 1999, 73-78.

*Primary Examiner*—Kaj K Olsen
(74) *Attorney, Agent, or Firm*—St. Onge Steward Johnston & Reens LLC

(57) ABSTRACT

The invention relates to an electrochemical gas sensor having both a reference sensor and an active sensor, whereby each reference and active sensor includes a substrate, a counter electrode deposited on a surface of the substrate, a sensing electrode also deposited on the surface, and a solid electrolytic material in electrical contact with both electrodes for carrying a flow of ions between them, which measures a concentration of a gas and compensates for relative humidity differences between sample gas and surrounding atmosphere. The sensor also includes a layer of solid electrolytic material on the sensing electrode of the reference sensor and a film of solid electrolytic material on the sensing electrode of the active sensor, whereby the layer is thicker than the film. The invention may further include a reference electrode in both the reference and active sensors for improving sensor accuracy and/or repeatability.

21 Claims, 5 Drawing Sheets

U.S. PATENT DOCUMENTS

| | | | |
|---|---|---|---|
| 5,273,640 A | 12/1993 | Kusanagi et al. | 204/404 |
| 5,514,253 A | 5/1996 | Davis et al. | 205/782.5 |
| 5,716,506 A | 2/1998 | Maclay et al. | 204/424 |
| 5,746,899 A | 5/1998 | Finbow et al. | 204/415 |

* cited by examiner

ELECTROCHEMICAL SENSOR COMPENSATED FOR RELATIVE HUMIDITY

CROSS REFERENCE TO RELATED APPLICATIONS

This application is a continuation patent application of U.S. patent application Ser. No. 10/029,626 for "An Electrochemical Sensor Compensated For Relative Humidity," filed Oct. 22, 2001, now U.S. Pat. No. 6,955,750

FIELD OF THE INVENTION

The invention relates to an electrochemical sensor for detecting a gas in a mixture of gases. More particularly, the invention is an electrochemical sensor that detects the presence of a gas while compensating for the relative humidity of surrounding gases.

BACKGROUND OF THE INVENTION

Monitoring toxic gases is a great concern in relation to environmental pollution, occupational health, and industrial emission control. Known methods and apparatuses have been developed to detect the presence of gases. For example, gas chromatography, ion chromatography, electrolytic conductivity detection, and conductometric measurement are typically used to detect gases. However, these manners for detecting gases have generally been expensive, cumbersome, and shown to have low sensitivities and slower response times.

Electrochemical sensors were provided to overcome these limitations. Electrochemical sensors typically operate at room temperature, provide signals which vary linearly with concentrations of analyte species, have improved response times, and exhibit acceptable sensitivity with high durability. In addition, electrochemical sensors are compact and can be used for continuous monitoring.

Electrochemical gas sensors usually detect the presence of gases with sufficient reliability and accuracy. However, if the humidity of the sample gas to be measured within the sensor is different than the humidity of the atmosphere surrounding the sensor, which is typically used to determine the baseline of the measurement, a sensor's accuracy may be compromised. The greater the difference in humidity, the less likely the sensor will accurately detect a gas.

U.S. Pat. No. 5,716,506 to Maclay et al. ("Maclay") discloses an electrochemical gas sensor that detects the presence of a gas while compensating for its dependence on the humidity in the gas. Maclay discloses an invention comprising a reference sensor and an active sensor. The reference sensor utilizes electrodes that are inert with respect to the gas being detected. Hence, the reference sensor is sensitive only to relative humidity and temperature of the surrounding air. The active sensor measures the gas and humidity while taking into account the temperature. The sensor response, which depends on relative humidity, is then compensated by subtracting the response of the reference sensor from the response of the active sensor.

A disadvantage of Maclay is that it does not compensate for the relative humidity difference between the sample gas and surrounding atmosphere. Moreover, no where does Maclay disclose compensating for relative humidity by varying the thicknesses of electrolytic material on the sensing electrodes of the active and reference sensors. In fact, the compensation of the relative humidity proposed by Maclay does not effectively compensate for the difference in humidity of the sample gas and the atmosphere, where the baseline measurement is performed. Moreover, Maclay does not disclose a manner for wetting the electrolytic material where it is known in the trade that sensor response is typically dependent upon humidity.

What is desired, therefore, is an electrochemical gas sensor which compensates for relative humidity differences between sample gas and the surrounding air. What is also desired is a sensor that compensates for relative humidity without directly measuring humidity. What is further desired is an electrochemical sensor that sufficiently hydrates the electrolytic material.

SUMMARY OF THE INVENTION

Accordingly, it is an object of the invention to provide an electrochemical gas sensor compensated for relative humidity.

It is another object of the invention to provide a sensor compensated for the difference in humidity between the surrounding atmosphere and gas being detected without measuring the humidity directly.

It is still another object of the invention to provide a sensor compensated for relative humidity by varying the thicknesses of electrolytic material on the sensing electrodes of both the active and reference sensors.

These and other objects of the invention are achieved by an electrochemical gas sensor having both a reference sensor and an active sensor, whereby each reference and active sensor includes a substrate, a counter electrode deposited on a surface of the substrate, a sensing electrode also deposited on the surface, and an electrolytic material in electrical contact with both electrodes for carrying a flow of ions between them. The sensor also includes a layer of electrolytic material on the sensing electrode of the reference sensor which is different in thickness from the film of electrolytic material on the sensing electrode of the active sensor.

The electrochemical gas sensor may further include a reference electrode in both the reference and active sensors for improving accuracy and/or repeatability. The reference electrode is also in electrical contact with the electrolytic material for permitting the establishment of a stable reference potential.

The electrochemical gas sensor may also include a solution in contact with and for wetting the electrolytic material in order to improve sensor sensitivity. The sensor may further include a reservoir for containing the solution.

In an alternative embodiment, the electrochemical gas sensor includes both a reference sensor and an active sensor, whereby each reference and active sensor further includes a substrate, a counter electrode deposited on a surface of the substrate, a sensing electrode also deposited on the surface, and an electrolytic material in electrical contact with both electrodes for carrying a flow of ions between them. The sensing electrode of the active sensor is of a different material than the sensing electrode material of the reference sensor. In this alternative embodiment, the reference sensor's sensing electrode is made of a material that is less responsive to the gas being detected than the material of the active sensor's sensing electrode.

In other embodiments, the material of the reference sensor's sensing electrode is inert to the gas being detected. In certain other embodiments, Gold, a material inert to the gas being detected, is used as material for the reference sensor's sensing electrode. The active sensor's sensing electrode is made of a material responsive to the gas being detected, such as Platinum.

The electrochemical gas sensor further includes a solution, and reservoir for containing the solution, for wetting the electrolytic material to reduce the humidity dependence and, thus, improve sensor sensitivity.

In an alternative embodiment, the electrochemical gas sensor includes two sensing electrodes sharing a common counter and reference electrode, whereby each sensing electrode further includes different thicknesses of an electrolytic material for compensating for relative humidity.

The invention and its particular features and advantages will become more apparent from the following detailed description considered with reference to the accompanying drawings.

DETAILED DESCRIPTION OF THE DRAWINGS

Figure 1:
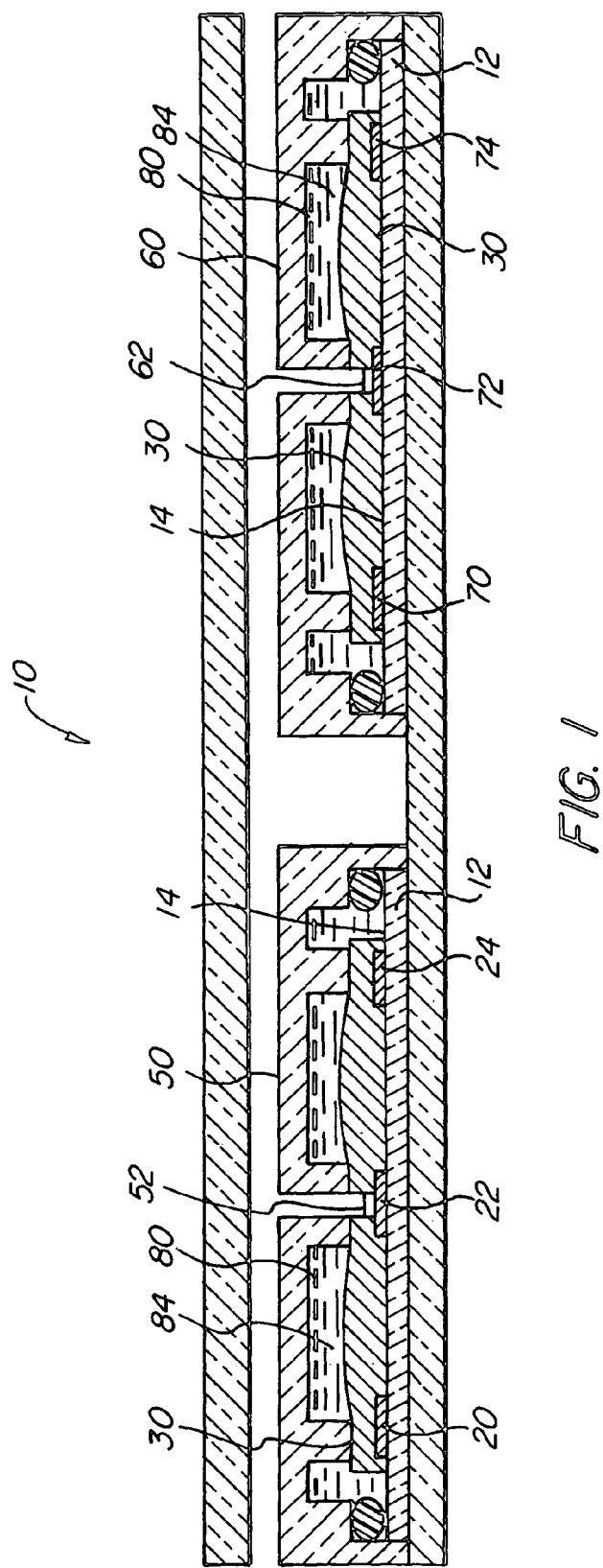
FIG. 1 depicts the electrochemical gas sensor in accordance with the invention.

FIG. 1 depicts the electrochemical gas sensor 10 in accordance with the invention. Electrochemical gas sensor 10 comprises two sensors, reference sensor 50 and active sensor 60, each of which is constructed the same and has the same limitations as the other except for having different thicknesses of electrolytic material 52 and 62 on the sensing electrodes. Both reference and active sensors include a housing, a substrate, a surface of the substrate for depositing electrodes thereon, electrolytic material for carrying ions between the electrodes, a first electrode, and a second electrode. Electrochemical gas sensor 10 operates to detect the presence of a particular gas while compensating for relative humidity by wetting the electrolytic material to reduce humidity dependence. Sensor 10 further compensates for relative humidity without directly measuring it.

Sensor 10 detects the presence of a desired gas in an unknown mixture of gases by taking the difference between a measurement of current between first and second electrodes, 20 and 22, of reference sensor 50 and a measurement of current between first and second electrodes, 70 and 72, of active sensor 60. The measurement of current is indicative of the concentration of a gas present. electrolytic material 30 is in contact with both first and second electrodes of each sensor and acts as a conductive medium to carry ions from the first electrode to the second electrode, or vice versa.

As depicted in FIG. 1, first electrode 20 is the counter electrode and second electrode 22 is the sensing or working electrode. However, first and second electrodes, 20 and 22, are interchangeable and second electrode 22 may be the counter electrode whereas first electrode 20 may be the sensing electrode. The same is true of first and second electrodes, 70 and 72, of active sensor 60.

First electrode 20 and second electrode 22 include any known or novel conductive material suitable for conducting electricity. Generally, a metallic material, such as Platinum, is used but any material permitting a measurement of current between the electrodes suffices. The electrodes are applied using known or novel methods for applying thin films, including spin/sputter coating or evaporating the electrodes onto surface 14. Besides spin/sputter coating, the electrodes may also be deposited using photolithography.

In addition, reference sensor 50 and active sensor 60 may each further include a third electrode deposited on surface 14. Third electrode 24 on reference sensor 50 and third electrode 74 on active sensor are not necessary for proper functioning of electrochemical gas sensor 10 but provide a more desirable sensor because sensitivity, accuracy, selectivity, and/or repeatability are improved. Third electrodes 24 and 74, acting as reference electrodes, provide a stable reference potential for setting the sensing electrode potential at which the current between the counter and sensing electrodes is measured with higher reproducibility and stability. The third electrodes, or reference electrodes, include all the limitations of both the first and second electrodes and may further be interchanged with either of them. However, for the purposes of FIG. 1, third electrodes 24 and 74 are depicted as the reference electrodes.

Substrate 12 includes known or novel materials used for forming the housing of electrochemical gas sensor 10 and the supporting surface 14 upon which first and second electrodes, 20 and 22, are deposited. The substrate has a surface that is generally, although not necessarily, flat so that a desirably thin film of conductive material may be deposited thereon free from unnecessary pores or crevices. Suitable materials include glass or any nonconductive material so as not to cause an electrical short circuit between the electrodes. Such a material may be classified as an insulating material.

Solid state electrolytic materials are advantageous in that they permit the thickness of the electrolytic layer to be less than an electrolytic layer in a liquid state. Said electrolytic material 30 is approximately between 0.0002 and 0.04 inches thick. The preferred range is approximately between 0.007 and 0.010 inches thick but may vary depending on the desired performance of the sensor. The thinner the electrolytic layer, the quicker the gas diffuses through the layer and the quicker the response time. Said electrolytic material 30 includes Nafion or any ionically conductive material.

However, if a solid state or dry said electrolytic material is used, it needs to be wetted in order to improve sensor sensitivity and decrease its dependence on humidity. Dry said electrolytic materials are known to have poor electrically conductive properties.

Hence, solution 84 functions to improve the sensor's sensitivity by wetting said electrolytic material 30. Solution 84 includes liquid electrolyte, water, or an acid solution. Solution 84 is contained in reservoir 80 within sensor 10. However, a controlled wetting is desired because flooding the electrolytic material causes the electrodes to be flooded. Flooding the electrodes with solution 84, particularly at the sensing electrode's surface, negatively affects sensor sensitivity and increases response time.

As shown in FIG. 1, said electrolytic material 30 further includes thin film 62 of a conductive medium in contact with the sensing electrode of active sensor 60 and thin layer 52 of a conductive medium in contact with the sensing electrode of reference sensor 50. Thin film 62 and thin layer 52 provide improved sensitivity because it increases the contact areas between the gas, said electrolytic material 30, and electrodes. Moreover, because thin film 62 and thin layer 52 have thicknesses less than said electrolytic material 30, response time and gas diffusion is enhanced. Thin film 62 and thin layer 52 are made of the same material as said electrolytic material 30 or any ion conductive material.

Where the humidity of the gas being measured is different than the humidity of the atmosphere surrounding sensor 10, a measurement of current may provide inaccurate indications as to the concentration of the gas because humidity affects current measurements. Furthermore, because humidity is a variable that cannot be controlled by sensor 10, sensor 10 compensates for relative humidity without actually measuring the humidity directly. Hence, sensor 10 eliminates the uncertainty, or error, when compensating for relative humidity because the humidity is not actually being measured.

Figure 2:
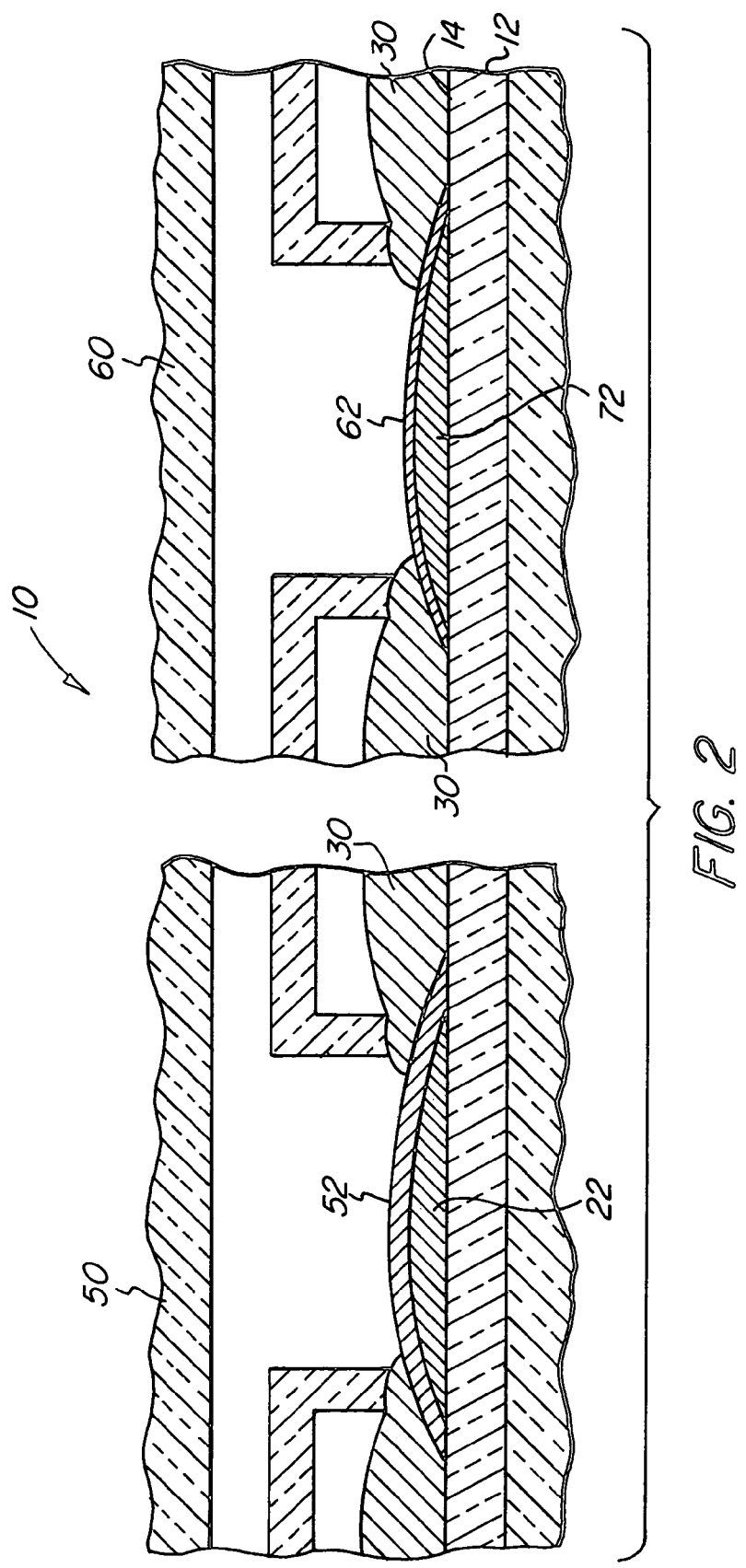
FIG. 2 more particularly depicts the electrolytic material placed over the sensing electrodes of the electrochemical gas sensor.

Sensor 10 compensates for relative humidity without directly measuring the humidity by having thin layer 52 of said electrolytic material on sensing electrode 22 of reference sensor 50 being of a different thickness than film 62 of said electrolytic material 30 on sensing electrode 72 of active sensor 60. This is more particularly depicted in FIG. 2. Because gas must diffuse through said electrolytic material 30, and more particularly layer 52 and film 62, in order to be detected, varying the thickness of said electrolytic material 30 affects the amplitude of the response signal of sensor 10. Following this concept, the invention utilizes the effect on the amplitude of the response signal to provide a mathematical determination of the detected gas compensated for relative humidity. Moreover, the mathematical determination is desirably independent of any measurement of relative humidity. Using hydrogen disulfide as an example of gas to be detected and where layer 52 is 10 times thicker than film 62, the mathematical determination is as follows:

Sensor 1 (thin Nafion coating): 100% $H_2S + RH_1 - RH_2$

Sensor 2 (10 times thicker Nafion coating): 10% $H_2S + RH_1 - RH_2$

Differential measurement (Sensor 1–Sensor 2): 90% $H_2S$ $RH_1$ is the relative humidity of the sample gas and $RH_2$ is the relative humidity of the surrounding air or gas used for baseline measurement. Because humidity is not being measured, the invention, therefore, eliminates any error associated with a humidity measurement. As shown in FIG. 1, layer 52 is approximately between 2.5 and 30 micrometers thick. Film 62, being 10 times thinner, is approximately between 0.25 and 3 micrometers thick.

So long as layer 52 and film 62 are of different thickness, sensor 10 detects the presence of a gas while compensating for the relative humidity. Preferably, but not necessary for proper function of sensor 10, layer 52 is at least 10 times thicker than film 62. In another embodiment, layer 52 is 20 times thicker than film 62. Therefore, layer 52 is approximately between 10 and 60 micrometers thick, whereas film 62 is approximately between 0.5 and 3 micrometers thick. The mathematical formula will therefore be as follows:

Sensor 1 (thin Nafion coating): 100% $H_2S + RH_1 - RH_2$

Sensor 2 (20 times thicker Nafion coating): 5% $H_2S + RH_1 - RH_2$

Differential measurement (Sensor 1–Sensor 2): 95% $H_2S$

In another embodiment, layer 52 is orders of magnitude thicker than film 62 and the mathematical formula will change correspondingly. The reasoning is that large variances in thicknesses between layer 52 and film 62 provide large differences in gas diffusion through said electrolytic material 30. This is desirable because as the difference in thickness between layer 52 and film 62 increases, the differential measurement between the active and reference sensors' readings approaches 100%. As the difference in readings approach 100%, the more accurate sensor 10 becomes while compensating for relative humidity, and the lower the standard of deviation and/or error in the readings become. Hence, although a preferred difference in the thicknesses of layer 52 and film 62 is that layer 52 be at least 10 times thicker, any difference in thicknesses suffices. The lower the difference in thicknesses, the greater the standard of deviation and/or error.

Figure 3:
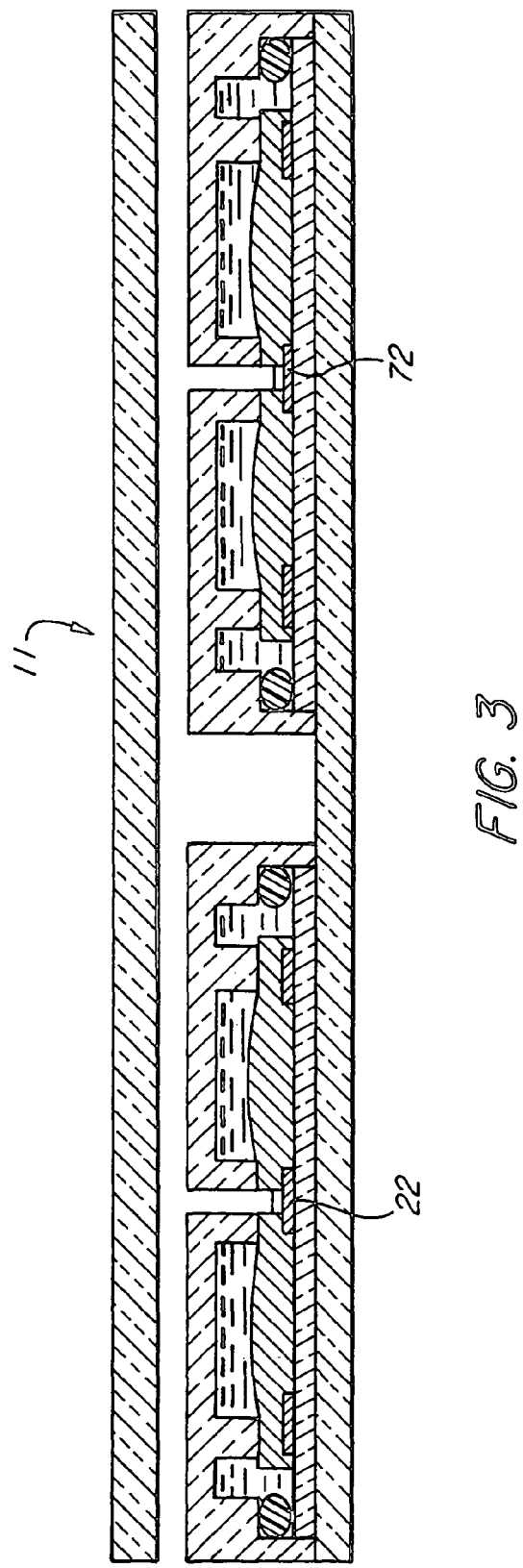
FIG. 3 depicts an alternative embodiment of the invention where the sensing electrodes are made of different materials.

In the alternative embodiment shown in FIG. 3, sensing electrode 22 is of a different material than sensing electrode 72. Sensing electrode 22 is made of a material that has less of a response to the gas being detected as sensing electrode 72 or may be inert to the gas being detected. Gold is a possible candidate for sensing electrode 22. Sensing electrode 72 is Platinum or other metallic material. A material responsive to a gas is defined to be any material having an electrochemical reaction when in contact with the gas and said electrolytic material, including layer 52 and film 62.

Similar to the embodiment depicted in FIG. 1, the more unresponsive to gas sensing electrode 22 becomes and the more responsive to gas sensing electrode 72 becomes, the more the difference between the active and reference sensors approaches 100% and the more accurately sensor 11 compensates for relative humidity.

In this embodiment, varying electrode materials accomplishes the same goal as varying thicknesses of layer 52 and film 62 of FIG. 1. In other words, various electrode materials respond differently to a gas due to differences in their electrocatalytic properties or the number of electron exchanges at the sensing electrode per molecule of gas of interest. In this embodiment, it is not required that sensing electrode 22 is made of gold and sensing electrode 72 is made of Platinum. All that is pertinent is that one sensing electrode material has less of a response to the gas being detected than the other sensing electrode material and that they respond similarly to relative humidity changes. Also, having different thicknesses of layer 52 and film 62 is unnecessary. Hence, layer 52 and film 62 may be of the same thickness when using different materials for sensing electrode 22 and sensing electrode 72.

Figure 4A:
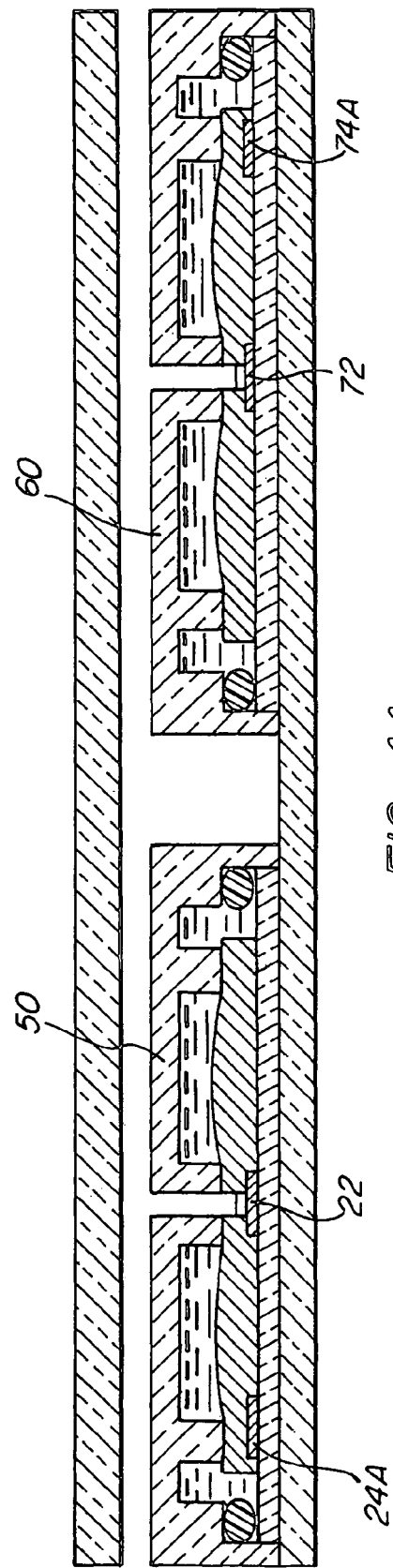
FIG. 4a depicts an alternative embodiment of the invention where each active and reference sensor has a counter and reference electrode that are combined.

FIG. 4a depicts an alternative embodiment where each active sensor 60 and reference sensor 50 has a counter and reference electrode that are combined. The counter/reference electrode 24A of reference sensor 50 and the counter/reference electrode 74A of active sensor 60 facilitates manufacturing and reduces development costs without sacrificing functioning of the invention. As the name implies, the counter/reference electrodes acts as both a reference point and a counter electrode. It should be known that counter/reference electrode 24A and counter/reference electrode 74A include all the limitations of the separately depicted counter and reference sensors described and depicted under FIG. 1. The embodiment further includes a thin layer 52 said electrolytic material on sensing electrode 22 and a thin film 62 of said electrolytic material on sensing electrode 72. Film 62 and layer 52 include all the limitations as described above under FIG. 1. Similar to the embodiment described under FIG. 1, so long as film 62 and layer 52 are of different thicknesses, sensor 11 detects the presence of a gas while compensating for the relative humidity.

Figure 4B:
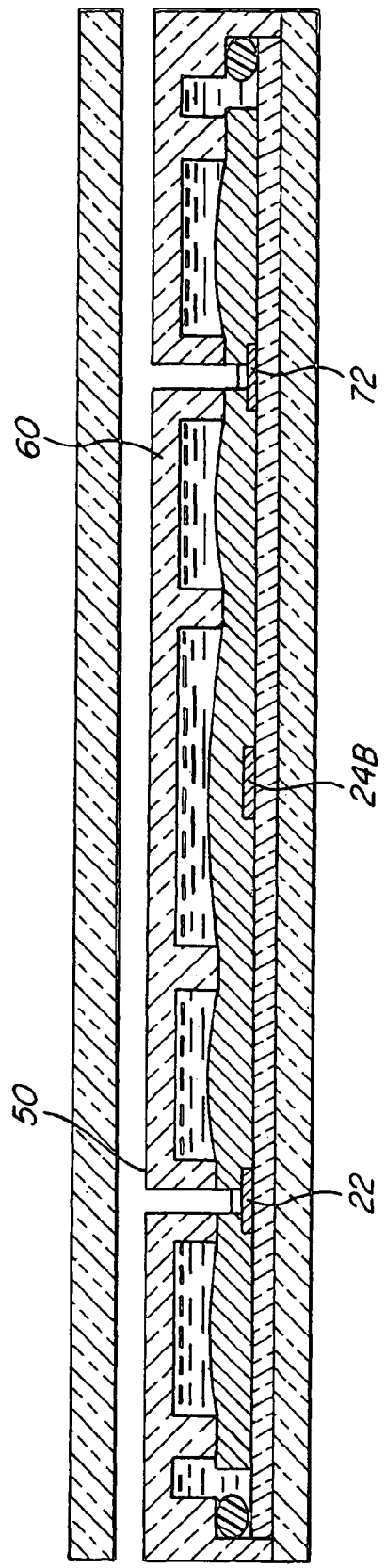
FIG. 4b depicts an alternative embodiment of the invention where each active and reference sensor share a single electrode that acts as both a counter and a reference electrode.

FIG. 4b depicts another alternative embodiment where each active sensor 60 and reference sensor 50 shares a single electrode that acts as both a counter and reference electrode. Counter/reference electrode 24B includes all the limitations of counter/reference electrodes 24A and 74A as described under FIG. 4a.

Although the invention has been described with reference to a particular arrangement of parts, features, dimensions, and the like, these are not intended to exhaust all possible arrangements, dimensions, or features, and indeed many other modifications and variations will be ascertainable to those of skill in the art.

What is claimed is:

1. An electrochemical gas sensor comprising:
a substrate having a surface;
a reference sensor having a first counter electrode, first sensing electrode, and first reference electrode deposited on said surface;
an active sensor having a second counter electrode, second sensing electrode, and second reference electrode deposited on said surface, said reference sensor and said active sensor being spaced apart from one another;
a first electrolytic material having a first thickness and being in contact with said first sensing electrode for carrying a flow of ions;
a second electrolytic material having a second thickness and being in contact with said second sensing electrode for carrying a flow of ions, said second thickness being less than said first thickness; and
additional electrolytic material in contact with active sensor and reference sensor, wherein said additional electrolytic material acts as a conductive medium to carry ions from the active sensor to the reference sensor.

2. The electrochemical gas sensor of claim 1, wherein said first and said second sensing electrodes are the same material.

3. The electrochemical gas sensor of claim 1, wherein said first and said second sensing electrodes are different materials.

4. The electrochemical gas sensor of claim 1, wherein said first sensing electrode includes a material inert to a gas.

5. The electrochemical gas sensor of claim 1, wherein said first sensing electrode includes gold.

6. The electrochemical gas sensor of claim 1, further comprising a reservoir in contact with said first electrolytic material on a side opposite of said substrate.

7. The electrochemical gas sensor of claim 6, further comprising a solution in said reservoir for hydrating said electrolytic material.

8. The electrochemical gas sensor of claim 1, wherein the first electrolytic material is between 10 and 60 micrometers thick.

9. The electrochemical gas sensor of claim 1, further comprising a solution for wetting the first electrolytic material and the second electrolytic material.

10. The electrochemical gas sensor of claim 1, wherein the second electrolytic material is between 2.5 and 30 micrometers thick.

11. The electrochemical gas sensor of claim 1, wherein the thickness of said additional electrolytic material is greater than the thickness of both the first electrolytic material and second electrolytic material.

12. The electrolytic gas sensor of claim 1, wherein the thickness of the additional electrolytic material is approximately between 0.0002 and 0.04 inches thick.

13. An electrochemical gas sensor comprising:
a first cell in communication with a second cell;
each cell having:
a substrate having a surface;
an electrode being deposited on said surface, said electrode being both a counter and reference electrode;
a first sensing electrode and a second sensing electrode, being spaced apart from one another and from said counter and reference electrode, being deposited on said surface;
a first electrolytic material in contact with said first sensing electrode for carrying a flow of ions;
a second electrolytic material in contact with said second sensing electrode for carrying a flow of ions; and
additional electrolytic material in contact with the first sensing electrode and the second sensing electrode, wherein the additional electrolytic material acts as a conductive medium to carry ions from the second sensing electrode to the first sensing electrode.

14. The electrochemical gas sensor of claim 13, wherein said first electrolytic material includes a first thickness.

15. The electrochemical gas sensor of claim 13, wherein said first electrolytic material includes a first thickness and said second electrolytic material includes a second thickness, said second thickness being less than said first thickness.

16. The electrochemical gas sensor of claim 13, wherein said first and said second sensing electrodes are the same material.

17. The electrochemical gas sensor of claim 13, wherein said first and said second sensing electrodes are different materials.

18. The electrochemical gas sensor of claim 13, further comprising a reservoir in contact with said first electrolytic material on a side opposite of said substrate.

19. An electrochemical gas sensor comprising:
a substrate having a surface;
three electrodes, said electrodes comprising a counter/reference electrode, a first sensing electrode and a second sensing electrode, said counter/reference electrode, said first sensing electrode and said second sensing electrode being spaced apart from one another and deposited on said surface of said substrate;
a first electrolytic material having a first thickness and being in contact with said first sensing electrode for carrying a flow of ions;
a second electrolytic material having a second thickness and being in contact with said second sensing electrode for carrying a flow of ions, said second thickness being less than said first thickness; and
additional electrolytic material in contact with the three electrodes, wherein the additional electrolytic material acts as a conductive medium to carry ions from the second sensing electrode to the first sensing electrode.

20. The electrochemical gas sensor of claim 19, further comprising a reservoir in contact with said first electrolytic material on a side opposite of said substrate.

21. The electrochemical gas sensor of claim 19, further comprising a solution in said reservoir for hydrating said electrolytic material.

* * * * *